(12) United States Patent
Meinert

(10) Patent No.: US 8,986,738 B2
(45) Date of Patent: Mar. 24, 2015

(54) INHALATIVE AND INSTILLATIVE USE OF SEMIFLUORINATED ALKANES AS AN ACTIVE SUBSTANCE CARRIER IN THE INTRAPULMONARY AREA

(75) Inventor: Hasso Meinert, Neu-Ulm (DE)

(73) Assignee: NOVALIQ GmbH, Heidelberg (DE)

( * ) Notice: Subject to any disclaimer, the term of this patent is extended or adjusted under 35 U.S.C. 154(b) by 219 days.

(21) Appl. No.: 12/415,482

(22) Filed: Mar. 31, 2009

(65) Prior Publication Data

US 2010/0008996 A1 Jan. 14, 2010

(30) Foreign Application Priority Data

Apr. 18, 2008 (EP) .................................. 08007640

(51) Int. Cl.
| | | |
|---|---|---|
| *A61K 38/02* | (2006.01) | |
| *A61K 38/16* | (2006.01) | |
| *A61K 47/06* | (2006.01) | |
| *A61K 9/14* | (2006.01) | |
| *A61K 9/00* | (2006.01) | |
| *A61K 31/07* | (2006.01) | |
| *A61K 31/135* | (2006.01) | |
| *A61K 31/137* | (2006.01) | |
| *A61K 31/192* | (2006.01) | |
| *A61K 31/196* | (2006.01) | |
| *A61K 31/355* | (2006.01) | |
| *A61K 31/513* | (2006.01) | |

(52) U.S. Cl.
CPC .............. *A61K 9/0073* (2013.01); *A61K 31/07* (2013.01); *A61K 31/135* (2013.01); *A61K 31/137* (2013.01); *A61K 31/192* (2013.01); *A61K 31/196* (2013.01); *A61K 31/355* (2013.01); *A61K 31/513* (2013.01)
USPC .............. 424/489; 424/45; 514/1.1; 514/759; 514/772

(58) Field of Classification Search
CPC ... A61K 9/0073; A61K 31/07; A61K 31/135; A61K 31/192; A61K 31/355
USPC ....................... 424/489, 45; 514/1.1, 759, 772
See application file for complete search history.

(56) References Cited

U.S. PATENT DOCUMENTS

| | | |
|---|---|---|
| 6,262,126 B1 | 7/2001 | Meinert |
| 6,486,212 B2 | 11/2002 | Meinert |
| 6,585,957 B1* | 7/2003 | Adjei et al. ...................... 424/45 |
| 7,205,343 B2 | 4/2007 | Dellamary et al. |
| 2008/0019926 A1* | 1/2008 | Krafft et al. ...................... 424/45 |

FOREIGN PATENT DOCUMENTS

| | | |
|---|---|---|
| EP | 0 965 334 | 3/2002 |
| KR | 10-0457157 | 11/2004 |
| WO | WO 97/12852 | 4/1997 |
| WO | WO 97/38579 A1 | 10/1997 |
| WO | WO 2005/099718 | 11/2005 |
| WO | WO 2007/059968 A2 | 5/2007 |

OTHER PUBLICATIONS

Lehmler, H. et al. "Liquid ventilation—A new way to deliver drugs to diseased lungs?", Chemtech, Oct. 1999.
Broniatowski, M. et al. "Two-Dimensional Miscibility Studies of Alamethicin and Selected Film-Forming Molecules", J. Phys. Chem. B., 112, 2008, pp. 7762-7770.
Meinert et al. "Semifluorinated alkanes—A new class of compounds with outstanding properties for use in ophalmology." *Eur. J. of Ophthalmology*. vol. 10. No. 3. 2000. pp. 189-197.
Kim et al. "A new, heavier-than-water silicone oil: a solution of perfluorohxyloctane in polydimethylsiloxane." *Eur. J. of Ophthalmology*. vol. 15. No. 5. 2005. pp. 627-637.
Leach et al. "Perfluorocarbon-associated gas exchange (partial liquid ventilation) in respiratory distress syndrome: A prospective, randomized, controlled study." *Critical Care Medicine*. vol. 21. No. 9. 1993. pp. 1270-1756.
Clark et al. "Survival of Mammals Breathing Organic Liquids Equilibrated with Oxygen at Atmospheric Pressure." *Science*. vol. 152. 1966. pp. 1755-1756.
Kuhlen et al. "Interium report relating to the application of active substances by partial liquid ventilation with semifluorinated alkanes: resorption kinetics of ibuprofen." *International Search Report from Univ. Clinic of the TWTH Aachen*. Jun. 15, 2007.

* cited by examiner

*Primary Examiner* — Mina Haghighatian
(74) *Attorney, Agent, or Firm* — Merchant & Gould P.C.

(57) ABSTRACT

A medical aid for the direct transport of at least one drug into lung regions of a patient, wherein provided as the carrier for at least one active substance is at least one semifluorinated alkane in which the at least one active substance is purely physically dissolved in a homogeneous phase.

19 Claims, 2 Drawing Sheets

Figure 1:
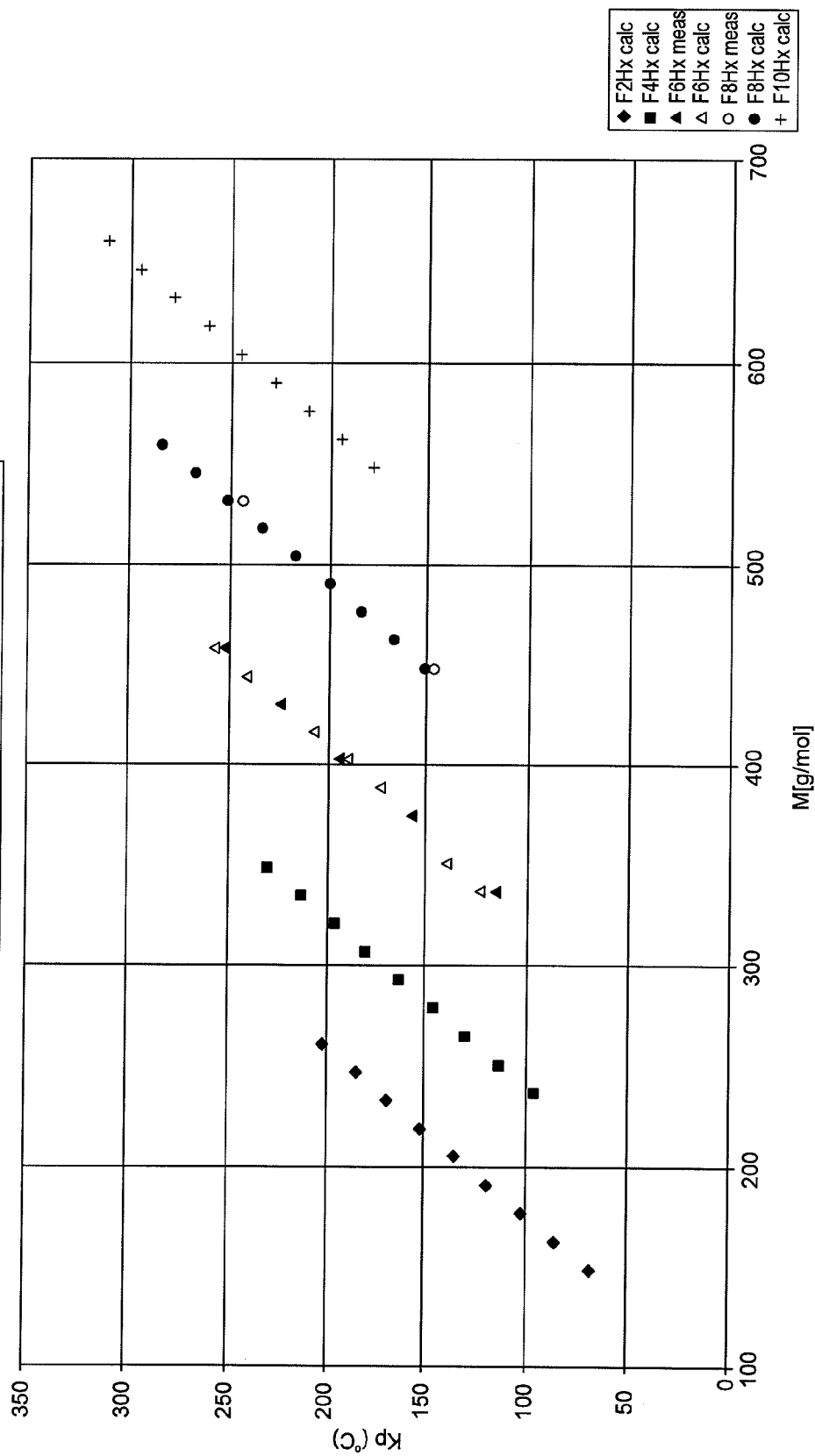

INHALATIVE AND INSTILLATIVE USE OF SEMIFLUORINATED ALKANES AS AN ACTIVE SUBSTANCE CARRIER IN THE INTRAPULMONARY AREA

This application is claims benefit of Serial No. 08 007 640.9, filed 18 Apr. 2008 in Europe and which application is incorporated herein by reference. To the extent appropriate, a claim of priority is made to the above disclosed applications.

BACKGROUND OF THE INVENTION

The health of human beings is increasingly being adversely affected by industrial dusts and waste gases, fine dusts, chronic bronchitis and emphysema of the lungs. The symptoms of severe acute lung failure are characterized by continuously pronounced disturbance in pulmonary gas exchange, an extreme drop in the compliance of the respiratory system and interstitial and alveolar lung oedema. Lethality is hitherto still specified at over 50%. One reason for that is the highly aggressive mechanical ventilation required to maintain approximately normal blood gases.

Perfluorocarbons 'PFCs', completely fluorinated carbon compounds, with a high level of solubility for oxygen but of very high density, have been used as therapeutic alternatives, for total liquid ventilation. That pure liquid ventilation however is technically difficult to implement. Therefore in the late Nineties partial liquid ventilation (PLV) by means of perfluorocarbons was clinically used for the first time. In that case, during normal gas ventilation, perfluorocarbon is intratracheally instilled bolus-wise to a maximum volume, corresponding to the functional residual capacity. The liquid is distributed in the lung due to the ventilation and standard gas ventilation can be continued with positive respiration pressures.

Semifluorinated alkanes 'SFAs' are known as medical aids for complete or partial liquid ventilation in surgical interventions, for inflating atelectasis lungs or collapsed lungs. In accordance with Dellamary et al active substances in the form of microballs can be dispersed by means of surfactants in fluorocarbons and intratracheally applied. Krafft et al. proposes an aqueous emulsion of phospholipids in fluorocarbons which, applied as an aerosol, is said to improve the fluidity of the natural lung surfactant.

The problem of the invention is to provide a medical aid with which drug transport into lung regions of a patient is achieved.

SUMMARY OF THE INVENTION

The invention provides a medical aid for the direct transport of at least one drug into lung regions of a patient, in which at least one semifluorinated alkane is provided as the active substance carrier. Preferably a straight-chain semifluorinated alkane of the general formula RFRH is used.

Semifluorinated alkanes of the type RFRH are compounds comprising a perfluorocarbon segment 'RF' and a hydrocarbon segment 'RH', wherein RF is a straight-chain or branched perfluoroalkyl group and RH is a straight-chain or branched, saturated hydrocarbon group. The compounds $F(CF2)_n(CH2)_mH$, with n and m=2 to 20, are liquid, colorless, water-insoluble, physically, chemically and physiologically inert. The boiling points correlate with the proportions by mass of the RF and RH segments in the molecule, see Table 1 and FIG. 2. SFAs are of densities of 1.1 to 1.7 g/cm$^3$, they have very low interfacial and surface tensions (about 45 and 19 mN/m respectively) and high vapor pressures (5 to 760 Torrs at 25° C.). SFAs have very high levels of gas solubility and an extremely high spreading capability, the latter being a multiple higher than that of PFCs.

The non-symmetrical RFRHs are amphiphilic compounds as a consequence of the lipophobic RF- and lipophilic RH-segment. Lipophilia rises with the length of the RH-part and conversely falls with an increasing RF proportion in the molecule. In comparison with non-polar PFCs, RFRHs, by virtue of their lipophilia, have a good dissolution capability for hydrocarbons and derivatives thereof, and thus also for many active substances or drugs. In that respect solubility in organic compounds increases in the RFRH, with an increasing RH-proportion. (In the situation of use the active substances in question must be used in their base form, that is to say not as hydrochlorides, phosphates or alkali salts which have been rendered water-soluble).

The active substances are dissolved in the solvent SFA purely physically in homogeneous phase, depending on the respective degree of distribution of <100 nm, in colloidal- to molecular-disperse fashion.

The following excellent properties of the invention result therefrom:
ensuring the gas exchange between the alveolar air and the blood flowing in the lung capillaries,
high interfacial activity due to low interfacial and surface tensions,
very high spreading capability,
carrier on the basis of the solubilities of hydrocarbons, their derivatives such as active substances and drugs.

The transport of active substances into the lung regions can be effected by way of:
inhalative application, and
partial or total liquid ventilation.
In that respect
active substances can be deposited in homogeneous dissolved form on the alveolocapillary membrane,
active substances can be transported by passage through the alveolar membrane into the blood flowing through the capillaries, or
harmful substances are removed from the lung surface.

By virtue of making use of the very large exchange area, active substances can be applied in that way, which is poorly possible or not possible at all in the conventional fashion, orally or by injection.

By virtue of the high levels of interfacial activity, mucuses clinging in viscous form on the alveolar surface are displaced out of the interface, which contributes to the therapy of mucovicidosis. The danger of asphyxiation due to mucous residues on the lungs of premature babies can also be reduced in that way. In addition the excellent spreading effect can be used for infiltration under or for penetrating into lung emphysema regions.

As is known, drugs which are distributed in powder form are involved in pulmonary application by means of current atomisation methods in the form of aerosols. Even if such an aerosol comprises a readily volatile PFC as propellent gas, this only involves a heterogeneous system comprising active substance particles, PFC droplets and possibly air. For, PFCs do not have any dissolution capability for hydrocarbons and their derivatives, and thus also not for drugs.

In oral application, those heterogeneous aerosols can reach the alveolar system only in a very small proportion, rather they are already previously retained in trachea and bronchial tubes.

BRIEF DESCRIPTION OF THE PREFERRED EMBODIMENT(S)

Figure 2:
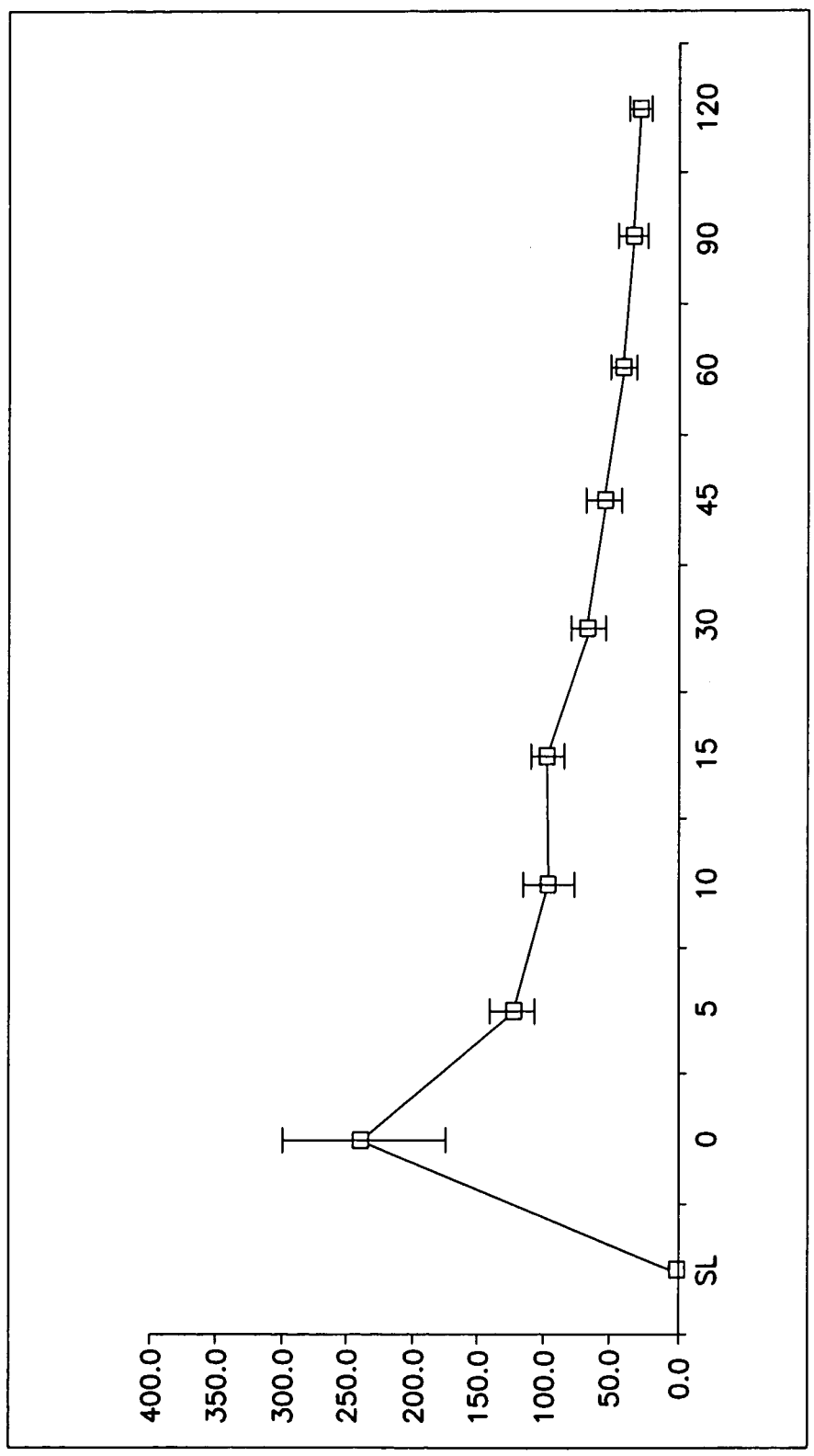

FIG. 1 is a graph of boiling points for diblock compounds at different concentrations; and
FIG. 2 is a graph of serum level over time.

DETAILED DESCRIPTION

Depositing Active Substances on the Alveolar System by Inhalative or Instigative Application The drugs described in accordance with the invention comprise homogeneous, colloidal-disperse solutions of active substances in the solvent RFRH, wherein the RH segments of the SFAs are associated with the hydrocarbon groupings of the active substance clusters and the RF segments are directed outwardly (9). The approximately spherical to elliptical micelles formed in that way are of an order of magnitude of 100 nm to 1 nm.

The concentration of the active substance is dependent on its solubility in the SFA and its RF/RH ratio. The more finely divided the substance to be dissolved is, and thus the greater its surface development, the correspondingly better is the enclosure with solvent molecules and thus also solubility.

In order to deposit the active substances on the alveolar membrane as quickly as possible, saturated, at least highly concentrated active substance solutions must be applied. In that way solubility of the active substance is exceeded and depositing thereof is thus achieved in a relatively short time, when exhaling the solvent.

The larger the molecule clusters are that are left behind, the correspondingly more probable is it that they remain on the membrane.

1. Inhalative Application in the Form of Aerosols

A solution of active substance in the SFA can be vaporized or purely physically or mechanically atomized by means of air, oxygen-enriched air or a gas mixture which maintains respiration. If RFRHs with a low boiling point or a high vapor pressure are used as solvents, see Table 1 and FIG. 2, they already act as a system-specific propellent gas at room to body temperature.

The proportion of the total of SFA+active substance and oxygen in the respiration gas is about 20 to in the extreme case 100%. Due to the high spreading capability of the SFAs, even primarily damaged, in particular atelectatic lung areas are reached in inhalative application. Of those micelles deposited on the alveolar membrane, in respiration the solvent molecules, by virtue of their vapor pressure which is high at body temperature, are successively exhaled while the active substances which are less readily volatile remain deposited.

2. Instillative Application in the Form of Solutions by Means of Partial Liquid Ventilation (PLV).

A solution of active substance in SFA can be applied boluswise by means of an endotracheal tube or a bronchoscope.

Larger amounts of active substance can be administered instillatively. By virtue of the larger total amount of applied solution, the exhalation process for the solvent lasts longer than with the aerosol application mode, in contrast more atelectatic lung areas can be reached with instillative application.

There are three pathways for inhalatively or instillatively deposited active substances:

They act as a drug on the membrane.
They are blocked with mucus and are thus expelled again.
They pass the membrane if their particle size <1 nm.

Active substances for inhalative or instillative application according to the invention with a deposit effect on the alveolar membrane are cytostatic agents, virostatic agents, bacterostatic agents, anti-asthmatic agents, antihistamine agents, proteins, in particular growth factors, peptides, vitamins and inter alia inflammation-inhibiting, bronchial-enlarging, and circulation-promoting drugs. Because of the required solubility in the SFA, the preferred representatives of the respective groups of active substances are those whose molecule structures have the lowest, outwardly acting polarity.

Transfer of Active Substances Through the Alveolocapillary Membrane

Besides the blood gas exchange necessary for life, different species can pass by way of the alveolar membrane into the bloodstream upon respiration. However substances can also be exhaled from the bloodstream by way of the membrane.

Thus it is known from blood substitute research that perfluorocarbons which previously were introduced into the bloodstream in emulsified form can be almost quantitatively exhaled by way of the lung.

In order to be able to transport active substances into the bloodstream in accordance with the invention, they must be defined by their physical-chemical properties, their molecule structure and a particle size in the nano range, of about 1 to 0.1 nm. As described hereinbefore fine distribution already occurs when the active substance is dissolved in the SFA.

A further reduction in size, if the active substances are still present as molecule clusters in the solvent, is effected by the action of physical methods such as an Ultra-Turrax homogeniser, a Gaulin shearing force homogeniser or ultrasound. Those energy feeds are linked to an increase in temperature, and therefore cooling must be effected during the homogenisation operation.

In order to exclude breakdown of the chemical composition of the active substances in those highly effective homogenisation methods, the procedure must be carried out under a protective gas and with constant monitoring. Enclosure with solvate molecules protects the substrate from reversible coagulation or Ostwald ripening, but the finished products should be stored in a cool condition. It is only thereafter that dosing with oxygen can be effected.

It is desirable for active substances which are already preproduced in the nano range or which are produced ab initio in the solvent SFA with that particle size to be used.

If the solvent is exhaled and the active substances deposited in very finely divided form on the membrane, the further transfer process is independent of whether inhalative or instillative application preceded it.

Provided that the solvate molecules relatively strongly adhere to the outer active substance layer, due to good stearic and physical-chemical interaction between solvent and substrate, active substances with a monolayer solvate casing can also be deposited.

The transit of the active substances through the alveolar membrane and absorption in the bloodstream or the plasma and further transport in the bloodstream is a time-diffusion-controlled process.

It is determined by the physical-chemical properties, the size and three-dimensional structure of the particles. The less complex the molecule bonds or molecules, the fewer steric impediments, the fewer polarising functional groups, the correspondingly easier is the passage. As described hereinbefore, very small active substances still encased with a monolayer of solvate molecules can be transferred. The prerequisite for that purpose is the shape and stability of those micromicelles. Those small particles are so encased with the solvate molecules that the RF-groups thereof are uniformly directed outwardly. That results in an overall species which is no longer polarisable and the passage of which is scarcely hindered.

The kinetics of the transfer process are thus controlled primarily by the particle size. The more the particles are molecularly dispersed, the correspondingly greater therefore is their surface development, and the correspondingly more effective is the interaction with the capillary forces acting at both sides at the membrane and thus the transfer situation.

The ultrapulmonary active substance transport claimed in accordance with the invention, into the bloodstream by means of semifluorinated alkanes, is highly suited for the drugs whose use is otherwise linked to frequent infection, subcutaneously, intramuscularly or intravenously. Intrapulmonary application is also for chronic diseases, the treatment of which by a recidivising medication is linked to drugs which are orally not available or which are poorly effective orally, or whose oral application leads to severe side-effects. Intrapulmonary transport also presents itself for the active substances which, because of their decomposability, would not withstand the gastrointestinal path.

Use of Semifluorinated Alkanes for the Transport of Active Substances in Total Liquid Ventilation (TLV)

The use of SFAs for total liquid ventilation is patented in Meinart. What is inventively novel and as described hereinbefore for the instillative PLV application, is that it is also possible with TLV to apply oxygen-saturated or partially saturated SFAs with dissolved active substances.

Such applications are particularly of interest when atelectatic lung regions are to be very rapidly reached or inflated, in total or substantially in total, and in that situation active substances are to be applied at the same time.

That concerns in particular mucus-loosening and antispasmodic, bronchial-enlarging, surface-active, inflammation-inhibiting or anti-ischaemic substances.

The detachment and removal of stubbornly adhering mucus from the lungs of premature babies and in the case of mucovicidosis, the removal of mucus-encased, inorganic and organic harmful substances and environmental pollutants, the removal of tarry deposits from the bronchial tubes and alveolae, inter alia, are examples of that form of application.

Intrapulmonary Use of Semifluorinated Alkanes in the Form of Aqueous w/o- or o/w-Emulsions as the Active Substance Carrier Meinart describes the use of SFAs for the production of aqueous o/w- or w/o-emulsions by means of biocompatible emulsifiers, with a given gas solubility.

What is inventive is that active substances for lung medicine are at the same time also soluble in such emulsions. In the case of the o/w-emulsions the active substances, instead of being used in their base form, can be better used in the form of the water-soluble hydrochlorides, phosphates or alkali salts.

Thus, by virtue of the solubility of drugs and by virtue of the simultaneous solubility of respiration gases in those systems, what is claimed is the use of those emulsions in combination with the active substances previously named for intrapulmonary application, for lung medicine. The o/w- or w/o-emulsions can be applied inhalatively as aerosols or instillatively as liquids.

Example 1

A solution of 6000 mg of ibuprofen in 1 L F6H8 was produced heat-sterilized as bulk material and made available for the clinical experiment on 7 pigs.

The results obtained demonstrate that the application of an SFA-ibuprofen solution by means of intratracheal instillation leads to rapid systemic resorption. With a blood volume of about 70 ml/kg KG in pigs more than 55% of the ibuprofen dissolved in SFA is already systematically resorbed within a few seconds. Toxic systemic secondary reactions did not occur.

Example 2

A saturated solution of 31,000 mg of alpha-tocopherol in 1 L F6H8 was produced heat-sterilized as bulk material. In the clinical experiment on pigs some of that solution was intratracheally instilled bolus-wise. In that case no transfer of the drug into the bloodstream was detected. After exhaling the SFA the drug remained in the alveolar region.

Example 3

A solution of 37,000 mg of retinol palmitate in 1 L F4H6 was produced heat-sterilized as bulk material and deposited under sterile conditions in 50 ml glass vessels. The content of those vessels can be applied either as an aerosol by means of pressure atomisers or intratracheally by means of a bronchoscope.

Example 4

A saturated solution of 30 mg of 5-fluorouracil in 1 L F6H8 is deposited by sterile filtration by means of 0.2 micrometre sterile filters in 20 ml glass vessels. The content of those vessels can be vaporized and inhalatively applied by means of known atomisation methods and with the devices known from anaesthesia for vaporising liquid anaesthetics, in aerosol form.

Example 5

Bromohexine is dissolved in F2H2 until saturation at 23° C. The solution is subjected to sterile filtering with cooling by means of 0.2 micrometre filters and deposited under sterile conditions in 20 ml vessels of glass or aluminium, with a nozzle and a pressure closure. Upon opening of the closure the solution is sprayed above +23° C. by the vapor pressure of the solvent, as a system-specific propellant, in aerosol form.

Example 6

Ibuprofen is dissolved at 25° C. until saturation occurs in 30% v/v F2H31 and 70% F2H3. The solution is subjected to sterile filtering and stored under sterile conditions in 20 ml vessels of glass or aluminium, equipped with a nozzle and pressure closure. Upon opening of the closure the content is sprayed above +35° C., due to the vapor pressure of the SFAs, in aerosol form.

Example 7

A solution of 120 mg of oseltamivir (Tamiflu®) in 1 L F4H6 is homogenized with the exclusion of substances in the atmosphere and under sterile conditions by means of ultrasound. Units at 20 ml in glass vessels are then heat-sterilized at 133° C.

Example 8

For the preparation of a w/o-emulsion 5% v/v water, 0.02 w/v ambroxol HCL, 5.0 w/v egg yolk lipid and 95% v/v F6H8 are homogenized with cooling by means of high pressure homogenisers. Thereafter the opaque emulsion is subjected to sterile filtration and stored in 10 ml units at +5° C. The emulsion can be applied inhalatively, sprayed by means of ultrasound as an aerosol, or instillatively, as a liquid.

LITERATURE (1) L C Clark, F Gollan: Science 152 (1966) 1755
(2) C L Leach et al: Crit. Care Med 21 (1993) 1270
(3) H Meinert: WO 97/12852 (1997)
(4) H Meinert: EP 0 965 334 B1
(5) H Meinert: U.S. Pat. No. 6,486,212 (2002)
(6) L A Dellamary et al: U.S. Pat. No. 7,205,343 B2 (2007)
(7) M P Krafft et al: WO/2005/099718 (2005)
(8) H Meinert, T Roy: Euro J Opthalmol 10 (2000) 189
(9) Y K Kim et al: Eur J Opthalmol 15 (2005) 627
(10) R Kuhlen, R Benzberg: Research report GB-FM 372037 RWTH Aachen Clinic/Novaliq Heidelberg

TABLE 1

Examples of semifluorinated alkanes of type RFRH and isomers thereof with boiling points (° C.):

| Compound | Abbreviation | Kp ° C. |
|---|---|---|
| CF3CF2CH2CH3 | F2H2 | 23 |
| $CF_3CF2(CH_2)2CH3$ | F2H3 | 60 |
| $CF_3CF2(CH_2)7CH3$ | F2H8 | 159 |
| $CF_3(CF2)2CH2CH3$ | F3H2 | 41 |
| $CF_3(CF2)2(CH_2)2CH3$ | F3H3 | 65 |
| $CF_3(CF_2)2(CH2)7CH3$ | F3H8 | 172 |
| $CF_3(CF_2)3CH_2CH3$ | F4H2 | 67 |
| $CF_3(CF_2)3(CH_2)3CH3$ | F4H4 | 129 |
| $CF_3(CF_2)3(CH_2)4CH3$ | F4H5 | 134 |
| $CF_3(CF2)3<CH_2)5CH3$ | F4H6 | 163 |
| $CF_3(CF_2)3(CH_2)6CH3$ | F4H7 | 184 |
| $CF_3(CF_2)3(CH_2)7CH_3$ | F4H8 | 196 |
| $CF_3(CF2)5CH_2CH3$ | F6H2 | 123 |
| $CF_3(CF2)5(CH_2)3CH3$ | F6H4 | 157 |
| CF3(CF2)5(CH2)5CH3 | F6H6 | 187 |
| $CF_3(CF_2)5(CH_2)7CH3$ | F6H8 | 223 |
| $CF_3(CF_2)5(CH2)iiCH_3$ | F6H12 | 290 |
| CF3CF2CH(CH3)2 | F2H3i | 36 |
| (CF3)2CFCH2CH3 | F3iH2 | 38 |
| $CF_3(CF2)2CH(CH_3)2$ | F3H3i | 60 |
| (CF3)2CFCH(CH3)2 | F3iH3i | 64 |

Kuhlen and Benzberg is a constituent part of the description of Example 1

International search report from the University Clinic of the RWTH Aachen, clinic for operative intensive medicine, director Prof. Dr R Kuhlen, project manager Dr R Bensberg.

Number of the research and development plan: GB-FM372037, commissioned by Novaliq GmbH Heidelberg, 15 Jun. 2007.

Interim Report Relating to the Application of Active Substances by Partial Liquid Ventilation with Semifluorinated Alkanes Resorption Kinetics of Ibuprofen 1. Introduction This study is therefore intended firstly to investigate the possibility of application of ibuprofen by means of PLV with SFA. For that purpose detection of the resorption kinetics in an intragroup comparison is formulated as the primary aim.

2. Material and Methods:

In accordance with the approval from the relevant authority (regional administration of Cologne, file No: 9.9310.50.203.2 CC 38, January 2007) the experiment was carried out on 7 pigs (female, Deutsche Landrasse, 29.3±1.8 kg body weight) under full anaesthesia.

Premedication was firstly effected with 4 mg/kg KG azaperone and 1 mg atropine subcutaneously, and after 20 minutes intramuscularly with 10 mg/kg KG ketamine. After a further 20 minutes a vein in the ear was perforated and an infusion applied. Introduction and continuation of the anaesthesia was effected in accordance with the criteria usual in human medicine (introduction with thiopental, intubation, respiration with 100% oxygen, continuation of the anaesthesia until the end of the experiment with a continuous application of fentanyl and thiopental). The depth of anaesthesia was controlled on the basis of the criteria usual in anaesthesia such as a rise in blood pressure and heart rate. The bladder was catheterized to drain off urine. Under sterile conditions, an arterial catheter was introduced using the Seldinger technique into the A. femoralis (to measure the arterial blood pressure and for arterial blood withdrawal) and a right heart catheter was introduced by way of an inlet device in the V. femoralis (for measuring central venous pressure, the pressure in the pulmonary artery, the heart time volume and for taking a blood sample from the pulmonary artery). The animals were firstly ventilated with a respiration volume of 8 ml/kg KG, a frequency of 20-30/min ($PaCO_2$ target value 30-40 mmHg), an inspiration/expiration ratio of 1:1 and a positively endexspiratory pressure of 5 mbars. A continuous infusion of an electrolyte solution of 0.1 ml/kg KG/min was begun with the beginning of catheterisation, to the end of the experiment.

After an initial measurement (BL; 'baseline') of all parameters (systemic and pulmonary haemodynamics, pulmonary gas exchange, ventilation parameters, arterial and mixed-venous blood gas analysis with haemoxymetry, arterial monitoring of the blood count, serum level ibuprofen) 5 ml/kg KG of a solution of SFA+6 g/l ibuprofen was intratracheally instilled in each case.

Thereafter all the above-mentioned parameters were respectively measured after 30, 60, 90 and 120 min, in addition the serum level of ibuprofen was ascertained in each case immediately after the instillation (0 min) and after 5, 10, 15 and 45 min.

3. Results:

All animals exhibited a stable state in terms of haemodynamics and gas exchange (see Table 1). The serum concentration of ibuprofen already reached its maximum value a few seconds after the instillation of the SFA-ibuprofen solution and then fell in a strictly monotonic fashion in the further period of observation (see FIG. 1).

4. Discussion/Conclusions:

The data obtained proved the hypothesis that an application of a saturated SFA-ibuprofen solution by means of intratracheal instillation leads to rapid systemic resorption of the ibuprofen. If the basic starting point adopted is a mean blood volume of about 70 ml/kg KG in the case of pigs of Deutsche Landrasse breed more than 55% of the ibuprofen dissolved in SFA was already systemically resorbed within a few seconds.

Besides demonstrating the suitability of SFA as a carrier for a systemic application of ibuprofen these results corroborated the hypotheses that SFA presents that carrier property also in relation to other active substances, and in the case of a non-saturated solution local application to the alveolae is also possible without systemic side-effects. In particular the latter could signify a novel and highly potent therapy option in the treatment of acute lung failure as for example highly effective active substances could be applied locally without potentially toxic systemic side-effects.

TABLE 1

| Gas exchange and haemodynamics | | | | | |
|---|---|---|---|---|---|
| | 0 min | 30 min | 60 min | 90 min | 120 min |
| HR | 100 ± 14 | 93 ± 10 | 87 ± 12 | 85 ± 11 | 84 ± 11 |
| MAP | 113 ± 12 | 122 ± 11 | 115 ± 9 | 116 ± 9 | 117 ± 14 |
| MPAP | 16.0 ± 4.7 | 18.9 ± 3.4 | 17.9 ± 3.4 | 17.0 ± 2.9 | 15.6 ± 2.4 |
| ZVD | 5.4 ± 2.8 | 4.3 ± 3.0 | 4.1 ± 2.5 | 4.1 ± 1.9 | 3.4 ± 1.5 |
| PCWP | 5.7 ± 2.8 | 5.4 ± 2.5 | 5.4 ± 2.4 | 5.1 ± 2.1 | 5.0 ± 2.4 |
| CO | 4.6 ± 0.9 | 4.4 ± 0.9 | 4.0 ± 0.7 | 3.9 ± 0.8 | 3.8 ± 0.6 |
| RR | 27.0 ± 0.6 | 27.1 ± 0.9 | 27.1 ± 0.9 | 27.1 ± 0.9 | 27.1 ± 0.9 |
| AMV | 6.2 ± 0.5 | 6.3 ± 0.3 | 6.3 ± 0.4 | 6.3 ± 0.4 | 6.3 ± 0.3 |
| PIP | 18.0 ± 1.3 | 19.7 ± 1.1 | 19.3 ± 1.0 | 18.9 ± 1.1 | 19.1 ± 1.5 |
| MIP | 10.4 ± 0.5 | 11.0 ± 0.6 | 11.0 ± 0.6 | 11.0 ± 0.6 | 11.0 ± 0.6 |
| $V_T$/KG | 7.8 ± 0.6 | 8.0 ± 0.5 | 7.9 ± 0.5 | 8.0 ± 0.5 | 8.0 ± 0.5 |
| $P_aO_2$ | 511 ± 33 | 346 ± 82 | 340 ± 64 | 341 ± 63 | 353 ± 40 |
| $P_aCO_2$ | 36.6 ± 3.8 | 34.0 ± 3.3 | 32.9 ± 3.4 | 32.5 ± 3.3 | 32.9 ± 3.7 |

HR (heart rate, $min^{-1}$);
MAP (mean arterial pressure, mmHg);
MPAP (mean pulmonary-arterial pressure, mmHg);
ZVD (central-venous pressure, mmHg);
PCWP (pulmonary-capillary wedge pressure, mmHg);
CO (heart minute volume, l/min);
RR (respiration rate, $min^{-1}$);
AMV (respiration minute volume, l/min);
PIP (peak inspiratory pressure, $cmH_2O$);
MIP (mean inspiratory pressure, $cmH_2O$);
$V_T$/KG (tidal volume per kg of body weight, ml);
$P_aO_2$ (arterial oxygen partial pressure, mmHg);
$P_aCO_2$ (arterial carbon dioxide partial pressure, mmHg).

The invention claimed is:

1. A medical composition configured for administering by direct transport of at least one drug directly into lung regions of a patient during inhalation, comprising:
   a carrier for at least one active substance, wherein the carrier is at least one semifluorinated alkane of the type RFRH, wherein RF is a straight chain or branched perfluoro alkyl group and RH is a straight chain or branched saturated hydrocarbon group, and wherein the composition comprises a solution at room temperature and wherein at least part of the carrier vaporizes at temperatures in the lung regions of a patient;
   wherein the length of each RF and RH segment is 2 to 20 carbon atoms, the at least one active substance being dispersed in the carrier as a colloid or molecular dispersion with a particle size of less than 100 nm at a concentration at which the active substance is configured to remain deposited when the semifluorinated alkane is exhaled; and
   wherein the at least one active substance is selected from the group consisting of mucolytic and antispasmodic, bronchial-enlarging, surface-active, antiinflammatory and antiischaemic substances, or wherein the at least one active substance is selected from the group consisting of the cytostatic agents, antiviral agents, bacteriostatic agents, antiasthmatic agents, antihistamines, antiinflammatory, bronchial-enlarging, circulation-enhancing medicaments, proteins, growth factors, peptides, and vitamins.

2. The composition according to claim 1, wherein the composition comprising the at least one active substance and semifluorinated alkane occurs in the form of micelles.

3. The composition according to claim 1, wherein the composition comprises an aerosol, the composition of the at least one active substance in the semifluorinated alkane is atomizable by air or by oxygen-enriched air or by a gas mixture which maintains respiration.

4. The composition according to claim 3, wherein the composition is in the form of an aerosol, and comprises a semifluorinated alkane, active substance and oxygen, wherein the composition forms about 20% to 100% of respiration gas.

5. The composition according to claim 1, wherein at least one active substance is depositable on an alveolar membrane, the composition comprising a semifluorinated alkane and the at least one active substance depositable on the alveolar membrane, wherein the semifluorinated alkane at body temperature is of a vapor pressure which causes the at least one active substance to remain deposited on the alveolar membrane during a successive inhalation.

6. The composition according to claim 1, wherein the composition is adapted for instillative application for active substance transport into a region of the lung that is atelectactic.

7. The composition according to claim 1, wherein the medical composition is penetrable into lung regions affected by emphysema.

8. The composition according to claim 1, wherein the medical composition comprises a mucoviscidosis therapy composition.

9. The composition according to claim 1, wherein at least one active substance is selected from the group consisting of expectorant, anti-spasmodic, bronchial-enlarging, surface-active, inflammation-inhibiting and anti-ischaemic substances.

10. The composition according to claim 1, wherein the active substance is selected from the group consisting of: cytostatic agents, virostatic agents, bacterostatic agents, anti-asthmatic agents, antihistamine agents, inflammation-inhibiting, bronchial-enlarging, circulation-promoting drugs, proteins, peptides and vitamins.

11. The composition according to claim 1, wherein the medical composition comprises an intrapulmonary transport of the at least one active substance into the bloodstream, the use of which is linked to the risk of subcutaneous or intramuscular or intravenous infection.

12. The composition according to claim 1, wherein the medical composition comprises an intrapulmonary transport into the bloodstream of at least one active substance for the treatment of chronic diseases, which for a recidivising medication, is orally not available, or orally poorly effective, or orally leads to severe side-effects.

13. The composition according to claim 1, wherein the medical composition comprises an intrapulmonary transport into the bloodstream of at least one active substance which suffers breakdown in the gastrointestinal path.

14. The composition according to claim 10, wherein the protein comprises a growth factor.

15. A method of depositing an active substance on a lung, comprising:
   selecting at least one active substance from the group consisting of mucolytic and antispasmodic, bronchial-enlarging, surface-active, anti-inflammatory and anti-ischaemic substances, or selecting the at least one active substance from the group consisting of the cytostatic agents, antiviral agents, bacteriostatic agents, antiasthmatic agents, antihistamines, anti-inflammatory, bronchial-enlarging, circulation-enhancing medicaments, proteins, growth factors, peptides, and vitamins; dispersing the at least one active substance in a carrier including a semifluorinated alkane, the composition comprising a colloid or molecular dispersion at room temperature with a particle size of less than 100 nm and at a concentration at which the active substance remains deposited on the surface of the lung and at least part of the carrier vaporizes at temperatures in the lung regions of a patient;

administering the composition comprising the dispersed active substance and the semifluorinated alkane being of the type RFRH, wherein RF is a straight chain or branched perfluoro alkyl group and RH is a straight chain or branched saturated hydrocarbon group with the length of each RF and RH segment being 2 to 20 carbon atoms, by directly transporting the composition to a surface of the lung during inhalation, and depositing the active substance on the surface of the lung when the semifluorinated alkane is exhaled.

16. The composition according to claim 1, wherein the active substance is dispersed in saturated form in the semifluorinated alkane.

17. The composition according to claim 1, wherein the active substance has a particle size in the range from 100 to 1 nm.

18. The composition according to claim 1, wherein the active substance is an organic substance.

19. The composition according to claim 1, wherein the active substance is dispersed in saturated or partially saturated form in the semifluorinated alkane.

* * * * *